US012622701B2

(12) United States Patent
Jalgaonkar et al.

(10) Patent No.: US 12,622,701 B2
(45) Date of Patent: May 12, 2026

(54) MULTI-SECTIONAL IMPLANT FOR VASCULAR TREATMENT

(71) Applicant: Balt USA, LLC, Irvine, CA (US)

(72) Inventors: Ujwal Jalgaonkar, Irvine, CA (US);
Ryan Solomon, Irvine, CA (US);
Stephanie Gong, Aliso Viejo, CA (US)

(73) Assignee: Balt USA, LLC, Irvine, CA (US)

( * ) Notice: Subject to any disclaimer, the term of this patent is extended or adjusted under 35 U.S.C. 154(b) by 0 days.

(21) Appl. No.: 18/787,796

(22) Filed: Jul. 29, 2024

(65) Prior Publication Data

US 2025/0032122 A1      Jan. 30, 2025

Related U.S. Application Data

(60) Provisional application No. 63/516,235, filed on Jul. 28, 2023.

(51) Int. Cl.
*A61B 17/12*      (2006.01)
*A61B 17/00*      (2006.01)

(52) U.S. Cl.
CPC .. *A61B 17/12113* (2013.01); *A61B 17/12145* (2013.01); *A61B 2017/00526* (2013.01); *A61B 2017/1205* (2013.01)

(58) Field of Classification Search
CPC .......... A61B 17/1214; A61B 17/12145; A61B 17/12113; A61B 17/12022; A61B 17/12031; A61B 17/221; A61B 17/2212; A61F 2230/0091
See application file for complete search history.

(56) References Cited

U.S. PATENT DOCUMENTS

| | | | |
|---|---|---|---|
| 6,808,380 | B1 | 10/2004 | Watanabe et al. |
| 8,182,506 | B2 | 5/2012 | Fitz et al. |
| 9,414,819 | B2 | 8/2016 | Fitz et al. |
| 9,717,500 | B2 | 8/2017 | Tieu et al. |
| 10,076,338 | B2 | 9/2018 | Fitz et al. |
| 2003/0219559 | A1 | 11/2003 | Schryver |
| 2013/0190801 | A1* | 7/2013 | Divino ...................... A61F 2/01 |
| | | | 606/200 |
| 2015/0359549 | A1 | 12/2015 | Lenker et al. |

(Continued)

FOREIGN PATENT DOCUMENTS

| | | |
|---|---|---|
| CN | 112826563 A | 5/2021 |
| EP | 2481552 A1 | 8/2012 |

(Continued)

OTHER PUBLICATIONS

European Patent Office, "International Search Report and Written Opinion," issued in related International Patent Application No. PCT/US2024/040075, mailed Oct. 22, 2024 (18 pages).

(Continued)

*Primary Examiner* — Majid Jamialahmadi
(74) *Attorney, Agent, or Firm* — The Marbury Law Group, PLLC

(57)      ABSTRACT

An implant for vascular treatment may include a wire having three or more sections, with adjacent sections having different stiffnesses and/or other properties to facilitate treating an aneurysm with a single instance of the wire. As compared to treating aneurysms using multiple coils, the wire having three or more sections may reduce the time required for treatment of the aneurysm.

16 Claims, 19 Drawing Sheets

(56)          References Cited

U.S. PATENT DOCUMENTS

| | | |
|---|---|---|
| 2016/0317158 A1 | 11/2016 | Lorenzo et al. |
| 2017/0367708 A1 | 12/2017 | Mayer et al. |
| 2021/0045749 A1 | 2/2021 | Wang et al. |

FOREIGN PATENT DOCUMENTS

| | | | |
|---|---|---|---|
| JP | 2019155737 A | 9/2019 | |
| JP | 2020146882 A | 9/2020 | |
| WO | 2023237739 A1 | 12/2024 | |

OTHER PUBLICATIONS

European Patent Office, "International Search Report and Written Opinion," issued in related International Patent Application No. PCT/EP2023/065486, mailed Sep. 8, 2023 (12 pages).
International Preliminary Report on Patentability, issued by the International Bureau, in related International Application No. PCT/US2024/040075, mailed Feb. 12, 2026 (11 pages).

* cited by examiner

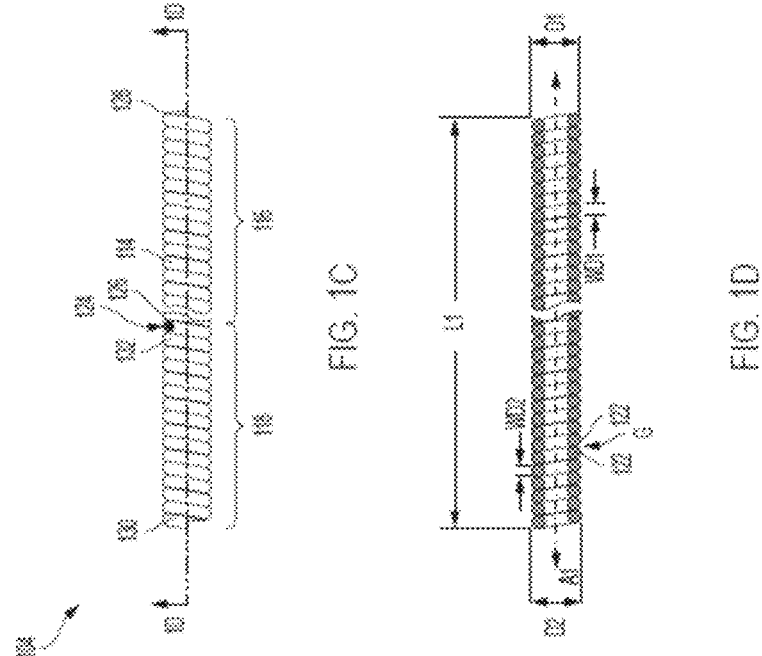

514

START

HEAT-SETTING A FIRST FILAR INTO A SHAPE DEFINING A FIRST VOLUME
672

ATTACHING A SECOND FILAR TO THE FIRST FILAR AND TO A THIRD FILAR
674

HEAT-SETTING A PRIMARY WINDING OF AT LEAST ONE OF THE FIRST FILAR, THE SECOND FILAR, OR THE THIRD FILAR
676

END

670

MULTI-SECTIONAL IMPLANT FOR VASCULAR TREATMENT

CROSS-REFERENCE TO RELATED APPLICATIONS

This application claims priority to and the benefit of U.S. Provisional Patent Application No. 63/516,235, filed on Jul. 28, 2023, the entire contents of which are hereby incorporated herein by reference.

BACKGROUND

Implantable medical devices can be used to treat a number of diseases and conditions associated with body lumens. For instance, weakening in the arterial wall can develop into vascular aneurysms and, ultimately, can lead to internal bleeding and/or other conditions. Implant devices can be used to occlude vessels, aneurysms, and other anatomical spaces to treat such potentially dangerous conditions and/or for vessel sacrifice. For example, implant devices can be used to obstruct (e.g., completely or partially) the flow in a blood vessel, such as, a location peripheral or adjacent to an aneurysm or other vascular abnormality. However, the time associated with accurate and stable placement of such implant devices at a treatment site is often critical. Accordingly, there is a need for implant devices that can be quickly and reliably placed for occlusion of vessels, aneurysms, and other anatomical locations.

SUMMARY

An implant for vascular treatment may include a wire having three or more sections, with adjacent sections having different stiffnesses and/or other properties to facilitate treating an aneurysm with a single instance of the wire. As compared to treating aneurysms using multiple coils, the wire having three or more sections may reduce the time required for treatment of the aneurysm.

According to an aspect, an implant for vascular treatment may include a wire having a first section, a second section, and a third section movable from a delivery state to a deployed state in response to removal of external pressure on the wire. In the delivery state, the first section, the second section, and the third section may collectively define a longitudinal axis with the second section longitudinally disposed between the first section and third section, and the second section of the wire may have stiffness differing from respective stiffnesses of the first section and the third section. In the deployed state, the first section may be securable to a target anatomical location of a subject with the first section defining a first volume and at least the second section packable into the first volume to occupy at least a portion of an anatomical vessel of the subject.

In certain implementations, the second section may be less stiff than the first section and is stiffer than the third section.

In some implementations, in the deployed state and in the absence of external pressure, the first volume of the first section may be in the shape of a box.

In certain implementations, in the deployed state, the second section may be packable into the first volume of the first section with the second section defining a second volume, and the third section is packable into the second volume of the second section within the first volume of the first section.

In some implementations, the first section may be positionable with the volume disposed in an aneurysm of the anatomical vessel, and the third section is a packable into a neck of the aneurysm.

In certain implementations, in the delivery state, the first section may be longer than the second section, and the second section is longer than the third section.

In some implementations, in the deployed state, the first section may include at least one loop defining the volume.

In certain implementations, the second section may have a proximal region and a distal region, the first section is coupled to the distal region of the second section at a first stress transition zone, the third section is coupled to the proximal region of the second section at a second stress transition zone. As an example, at least one of the first stress transition zone or the second stress transition zone may include a weld. Further, or instead, the implant may further include a sleeve crimped to the second section and at least one of the first section along the first stress transition zone or the third section along the second stress transition zone. Additionally, or alternatively, at least one of the first stress transition zone or the second stress transition zone may include glue, thread, or a combination thereof. Still further, or instead, the wire may have a wire diameter varying between at least two of the first section, the second section, or the third section. In certain instances, the wire may include primary windings along at least one of the first section, the second section, and the third section. As an example, in absence of external pressure on the primary windings, an outer diameter of the primary windings varies between at least two of the first section, the second section, or the third section. Additionally, or alternatively, the primary windings may define gaps therebetween, and the size of the gaps of the primary windings vary between at least two of the first section, the second section, or the third section.

In some implementations, modulus of rigidity of the wire varies between at least two of the first section, the second section, or the third section.

In certain implementations, the implant may further include a fourth section wherein, in the delivery state, the third section is disposed between the second section and the fourth section, and the fourth section is softer than the third section.

According to another aspect, a system for vascular treatment may include a catheter defining a lumen and a distal opening in fluid communication with one another; an implant including a wire having three or more sections coupled to one another and positionable in the lumen, and each adjacent pair of the three or more sections having stiffness varying therebetween; a tether coupled to the wire; and a pusher member detachably coupled to the wire via the tether, the pusher member advanceable in the lumen, advancement of the pusher member moving at least one of the three or more sections of the wire through the distal opening of the catheter to a deployed state defining a volume, into which at least another one of the three or more sections of the wire is packable to occupy at least a portion of an anatomical vessel of a subject.

According to yet another aspect, a method of fabricating an implant for vascular treatment may include heat-setting a first filar into a shape defining a first volume; and attaching a second filar to the first filar and to a third filar, the second filar differing in stiffness with respect to each of the first filar and the third filar, the first filar, the second filar, and the third filar respectively forming a first section, a second section, and a third section of a wire movable, in response to removal of external pressure on the wire, from a delivery state to a deployed state in which the first section is securable to a target anatomical location of a subject with the first section defining the first volume and at least the second section packable into the first volume.

In certain implementations, the first filar may have a first diameter, the second filar has a second diameter, and the third filar has a third diameter, and at least two of the first diameter, the second diameter, and the third diameter differ from one another.

In some implementations, the second filar may have a proximal portion and a distal portion, attaching the second filar to the first filar includes attaching the distal portion of the second filar to the first filar to form a first stress transition zone, and attaching the second filar to the third filar includes attaching the proximal portion of the second filar to the third filar to form a second stress transition zone.

In certain implementations, attaching the distal portion of the second filar to the first filar may include one or more of welding, gluing, tying, or crimping the first filar and the second filar to one another along the first stress transition zone.

In some implementations, attaching the third filar to the second filar may include one or more of welding, gluing, tying, or crimping the third filar and the second filar to one another along the second stress transition zone.

In certain implementations, the method may further include heat-setting a primary winding of at least one of the first filar, the second filar, or the third filar.

BRIEF DESCRIPTION OF THE DRAWINGS

FIG. 1C is a side view of the implant of FIG. 1A.

FIG. 1D is a cross-sectional side view of the implant of FIG. 1A, with the cross-section taken along 1D-1D in FIG. 1C.

Like reference symbols in the various drawings indicate like elements.

DESCRIPTION

Figure 1A:
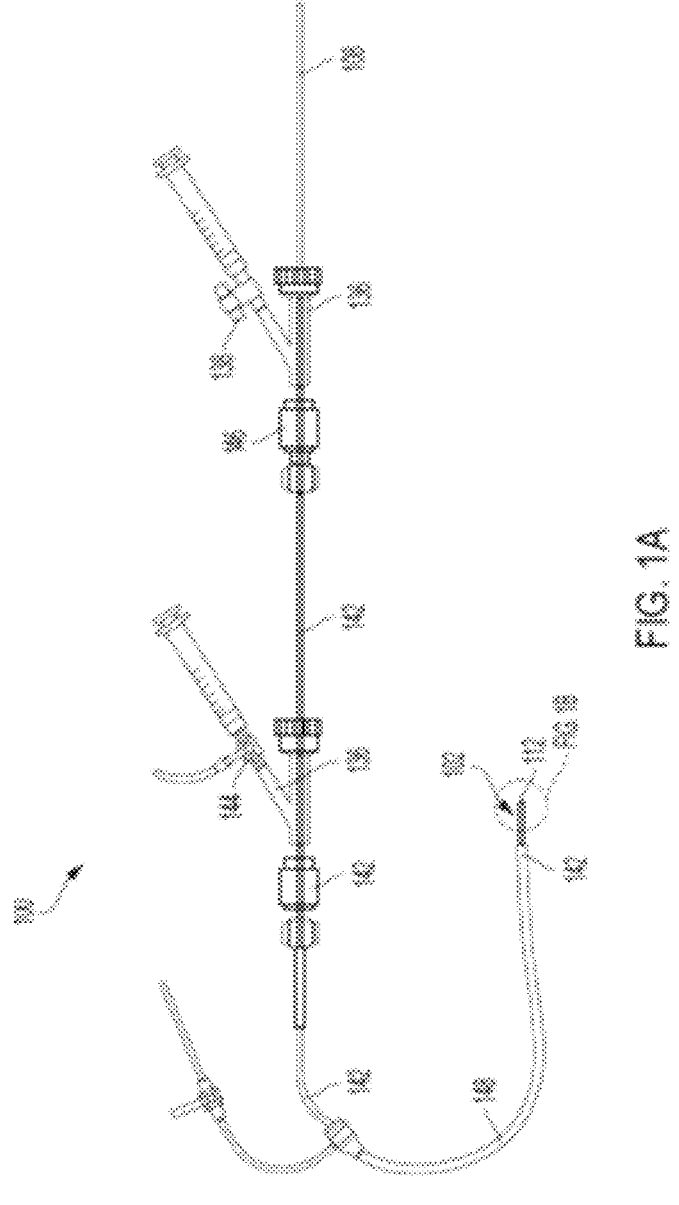
FIG. 1A is a schematic representation of a system for vascular treatment, the system including a catheter, an implant, a tether, and a pusher member.

Embodiments will now be described with reference to the accompanying figures. The foregoing may, however, be embodied in many different forms and should not be construed as limited to the embodiments set forth herein.

All documents mentioned herein are hereby incorporated by reference in their entirety. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and, similarly, the term "and" should generally be understood to mean "and/or."

Recitation of ranges of values herein are not intended to be limiting, referring instead individually to any and all values falling within the range, unless otherwise indicated herein, and each separate value within such a range is incorporated into the specification as if it were individually recited herein. The words "about," "approximately," or the like, when accompanying a numerical value, are to be construed as indicating a deviation as would be appreciated by one of ordinary skill in the art to operate satisfactorily for an intended purpose. Ranges of values and/or numeric values are provided herein as examples only, and do not constitute a limitation on the scope of the described embodiments. The use of any and all examples, or exemplary language ("e.g.," "such as," or the like) provided herein, is intended merely to describe the embodiments better and does not pose a limitation on the scope of the embodiments. No language in the specification should be construed as indicating any unclaimed element as essential to the practice of the embodiments.

In the following description, it is understood that terms such as "first," "second," and the like, are words of convenience and are not to be construed as limiting terms.

As used herein, unless otherwise indicated or made clear from the context, the term "physician" should be understood to include a surgeon or other interventional specialist preparing for and/or performing any one or more of the medical procedures described herein and, more broadly, should be understood to include any medical personnel, such as nurses, assisting a such surgeon or interventional specialist in preparing for or performing any one or more of the medical procedures described herein. Further, as used herein, the term "subject" shall be understood to include any type of mammal, including a human, on which a medical procedure such as, but not limited to a thrombectomy can be performed.

Further, as used herein, implants and portions thereof are described as having a "delivery state" and a "deployed state." It shall be appreciated that the "delivery state" refers to the shape and orientation of an implant or a portion thereof, as the context dictates, under external pressure, such as the pressure exerted by a catheter on the implant or a portion thereof disposed in a lumen defined by the catheter. Further, or instead, it shall be appreciated that the "deployed state" refers to the shape and orientation of an implant or a portion thereof, as the context dictates, as external pressure is removed from the implant or the portion thereof. Given that the shape and orientation of the implant in an anatomical vessel of a subject may become distorted in any of various different ways by external pressure on the implant from one or more anatomical features of the subject, the shape of the final shape of the implant in the anatomical vessel may be unpredictable and, thus, difficult to describe. Accordingly, for the sake of clear and efficient description, the deployed state of an implant or a portion thereof shall be understood to refer to the shape and orientation of an implant or a portion thereof, as the context dictates, in the absence of external pressure from the catheter and/or anatomical features of the subject. To the extent certain aspects of the deployed state of an implant are described in the context of the shape and orientation of the implant in the anatomical vessel, it shall be appreciated that such description assumes the implant is sized relative to the anatomical vessel to achieve certain characteristics of the implant in the deployed state in the absence of external pressure on the implant.

As used herein, the term "stiffness" shall be understood to refer to the ability of a part to resist plastic deformation and may be expressed as force required for unit deformation. Unless otherwise specified or made clear from the context, stiffness may depend on the geometry and the type of material (e.g., a material property such as modulus of rigidity) of a particular section of an implant. Further, or instead, the stiffness of a section of a given implant described herein may be expressed in relative terms with one section having a higher stiffness than another section and/or another section being softer than another section.

In the description that follows, implants are described as having a first section and a second section. It shall be appreciated that this is for the sake of clear and efficient description and should not be understood to be limiting, unless a contrary intent is explicitly indicated or is made clear from the context. Thus, any one or more of the implants of the present disclosure may have two or more section that are different from one another, as may be useful for achieving rapid and reliable placement of implants for vascular treatment.

Although the various embodiments disclosed herein with specific reference to vaso-occlusive devices (e.g., to block blood flow in specific vessels, to treat cerebral aneurysms and other vascular abnormalities, etc.), it shall be understood that this is for the sake of clear and efficient description. Thus, the implants, systems, and methods of the present disclosure shall be understood to be useful for other types of medical devices and/or other types of medical treatments, unless a contrary intent is explicitly indicated or made clear from the context. As an example, unless otherwise specified or made clear from the context, the implants described herein may be used with any size defect and/or to treat any indication, as desired or required. Further, while the present disclosure describes coil implants (e.g., microcoils) or other devices implantable (e.g., permanently, temporarily, retractably, etc.) within a vessel, it shall be appreciated that such implants may be implanted in other intraluminal structure, an aneurysm or other defect and/or any other location of a subject's anatomy. Further, while the implants are described as being delivered using a catheter, it shall be appreciated that the implants described herein may be delivered to and released at a target anatomical location of a subject using any desired protocol or technique.

Referring now to FIGS. 1A-IF, a system 100 for vascular treatment may include a catheter 102, an implant 104, a tether 106, and a pusher member 108. The catheter 102 may define a lumen 110 and a distal opening 112 in fluid communication with one another. The implant 104 may include a wire 114 having a first section 116 and a second section 118 each positionable in the lumen 110 of the catheter 102 in a delivery state. The tether 106 may be coupled to the second section of the implant 104, and the pusher member 108 may be detachably coupled to the second section 118 of the wire 114 via the tether 106. Further, or instead, the pusher member 108 may be advanceable in the lumen 110 in a distal direction toward the distal opening 112 of the catheter 102. In response to distal advancement of the pusher member 108 in the lumen 110, the first section 116 of the wire 114 may be movable through the distal opening 112 of the lumen 110 to a deployed state including at least one loop 120.

In general, the first section 116 of the wire 114 and the second section 118 of the wire 114 may differ from one another with respect to one or more properties or characteristics such that the first section 116 of the wire 114 and the second section 118 of the wire 114 may facilitate carrying out different aspects of vascular treatment using only a single implant. As compared to vascular treatment using multiple implants (e.g., multiple coils) to achieve differences in properties or characteristics, the differences in the properties or characteristics of the first section 116 of the wire 114 and the second section 118 of the wire 114 may facilitate carrying out vascular treatment using fewer implants (e.g., a single implant in some instances), thus reducing the time of an implantation procedure, simplifying an implantation procedure, improving safety and/or providing one or more other benefits or advantages.

In certain implementations, the first section 116 of the wire 114 may be stiffer than the second section 118 of the wire 114 such that a spring constant of the first section 116 of the wire 114 is greater than a spring coefficient of the second section 118 of the wire 114. For example, the spring constant of the first section 116 of the wire 114 may be greater than the spring constant of the second section 118 of the wire 114 by up to about 40%. Further, or instead, the first spring constant may be 2 to 20 times greater than the second spring coefficient). In certain implementations, the first section 116 of the wire 114 may have a first spring coefficient of greater than about 10 N/m and less than about 20 N/m, as may be useful for retaining shape to secure the first section 116 of the wire 114 to the target anatomical location. Further, or instead, the second section 118 of the wire 114 may have a second spring coefficient of greater than about 1 N/m and less than about 10 N/m, as may be useful for packing the second section 118 of the wire 114, in the deployed state, into a nonlinear shape to at least partially occupy an anatomical vessel with the first section 116 of the wire 114 secured to the target anatomical location. The greater stiffness of the first section 116 of the wire 114 in the deployed state may facilitate anchoring or otherwise securing the implant 104 within the target anatomical location of a subject while the lower stiffness of the second section 118 of the wire 114 in the deployed state may facilitate achieving a nonlinear shape to at least partially occupy an anatomical vessel with the first section 116 of the wire 114 secured to the target anatomical location. Additionally, or alternatively, the shape, size (e.g., diameter or other cross-sectional dimension, length, etc.) of the first section 116 of the wire 114 and the second section 118 of the wire 114 may differ from one another, as may be useful for carrying out vascular treatment using the wire 114.

In some implementations, in the deployed state, the first section 116 of the wire 114 may include at least one loop 120, as may be useful for circumscribing a target anatomical location within a vessel with radial force of the at least one loop 120 against the target anatomical location facilitating securing the implant 104 in place. In this context, the at least one loop 120 shall be understood to include any one or more revolution shapes upon release of external pressure on the first section 116 of the wire 114. That is, upon release of external pressure on the first section 116 of the wire 114, the at least one loop 120 does not necessarily need to be geometrically circular, provided that the shape of the at least one loop 120 facilitates securing the implant 104 at a target anatomical location within a subject to carry out the vascular treatment. While the at least one loop 120 may include complete revolutions, the at least one loop 120 may further, or instead, include partial loops (e.g., ¼, ½, ¾, etc.). As an example, the at least one loop 120 of the first section 116 of the wire 114 in the deployed state may include at least three loops (e.g., 3 to 3¼ loops) and, in some instances, the at least three loops may collectively form a helical shape.

The at least one loop 120 may have an outer diameter DIM B equal or substantially equal to an inner diameter of a target vessel (e.g., an anatomical vessel adjacent to a vascular abnormality, a section of the subject's vessel intended to undergo vessel sacrifice, etc.), with substantial equality in this context understood to allow for deviations of the anatomy from being uniformly circular in certain locations. In some embodiments, the outer diameter DIM B of the at least one loop 120 may be greater than the diameter of the target vessel (e.g., 0 to 1, 1 to 2, 2 to 3, 3 to 4, 4 to 5, 5 to 10% greater, more than 10% greater, percentages between the foregoing values and ranges, etc.). In such configurations, the first section 116 of the wire 114 may be sized, shaped, and/or otherwise adapted to exert a force on the target anatomical location to help anchor or secure the implant 104 within the target vessel. According to some implementations, DIM B may be modified or otherwise adjusted to accommodate particular design requirements and/or application or use. DIM B of the first section 116 of the wire 114 may be greater than about 2 mm and less than about 25 mm (e.g., 2 to 25, 3 to 20, 4 to 15, 5 to 10 mm, values between the foregoing, etc.), with allowances for dimensional tolerances associated with manufacturing. While the at least one loop 120 may be substantially circular in some instances, it shall be appreciated that the at least one loop 120 may be non-circular in other instances and, in instances in which the at least one loop 120 is non-circular, DIM B shall be understood to refer to a maximum outer dimension of the non-circular shape.

Figure 1B:
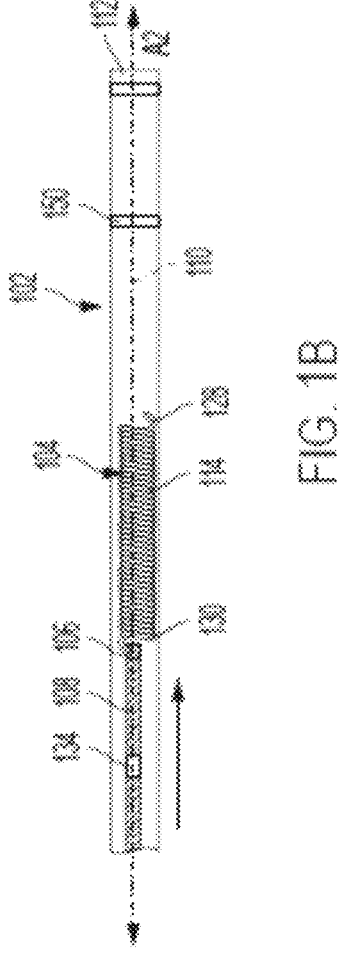
FIG. 1B is a schematic representation of a cross-section of a distal portion of the system of FIG. 1A as the pusher member moves the implant distally through the catheter.
Figure 1E:
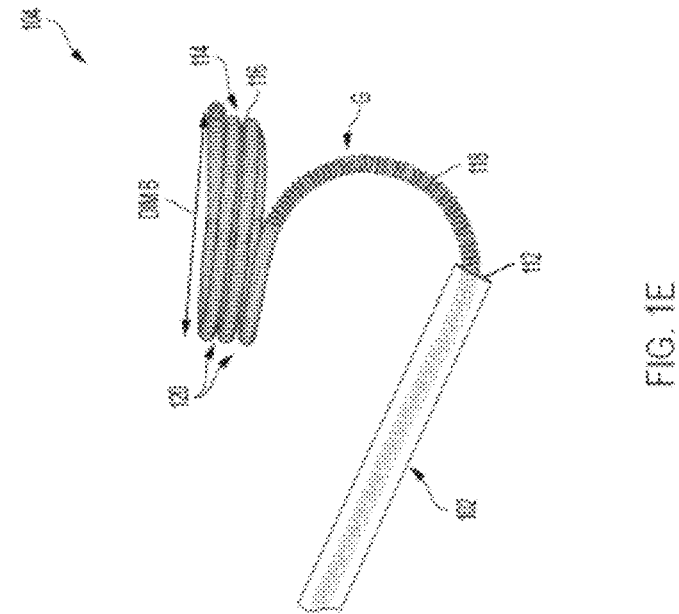
FIG. 1E is a schematic representation of a first section of a wire of the implant of FIG. 1A in a deployed state with a second section of the wire of the implant of FIG. 1A in the delivery state in the catheter.

In general, the first section 116 of the wire 114 may be movable from the delivery state (shown, for example, in FIG. 1B) in the lumen 110 of the catheter 102 to the deployed state as the second section 118 of the wire 114 remains in the delivery state in the lumen 110 of the catheter 102 (shown, for example, in FIG. 1E). Additionally, or alternatively, with the second section 118 of the wire 114 in the delivery state in the lumen 110 and the first section 116 of the wire 114 in the deployed state (shown, for example, in FIG. 1E), the pusher member 108 may be further advanceable in the distal direction toward the distal opening 112. In response to the further distal advancement of the pusher member 108 in the lumen 110 of the catheter 102, the second section 118 of the wire 114 may be movable through the distal opening to a deployed state including a nonlinear shape of the second section 118 of the wire 114.

In general, the second section 118 of the wire 114 may have any one or more of various different nonlinear shapes associated with carrying out the vascular treatment at the target location within the vessel of the subject. In particular, the nonlinear shape of the second section of the wire 114 in the deployed state may occupy at least a portion of the anatomical vessel. For example, in the deployed state of the wire 114 and with the first section 116 of the wire 114 secured to the target anatomical location, the second section 118 of the wire 114 may be packable onto itself to at least partially occupy the anatomical vessel. Stated differently, with the first section 116 of the wire 114 secured in place at the target anatomical location, the nonlinear shape of the second section 118 of the wire 114 may be packed onto itself such that the second section 118 of the wire 114 acts as a packing coil.

In certain implementations, the first section 116 of the wire 114 and/or the second section 118 of the wire 114 may include primary windings 122 defining a first longitudinal axis A1 circumscribed by the primary windings 122. The primary windings 122 may include a helically-wound member having sequential turns or winds. In some implementations, such turns or winds may be angled relative to the first longitudinal axis A1 and/or relative to a radial axis of the primary windings 122. For example, the turns or winds may be angled 0 to 90 degrees (e.g., 0 to 90, 10 to 80, 20 to 60 degrees, angles between the foregoing, etc.) relative to the first longitudinal axis A1 and/or the radial axis. Further, or instead, with the first section 116 of the wire 114 and the second section 118 of the wire 114 positioned in the delivery state in the lumen 110 of the catheter 102, the primary windings 122 may circumscribe a second longitudinal axis L2 defined by the lumen 110 of the catheter 102, as may be useful for delivering the implant 104 to the target anatomical location via the catheter 102.

The primary windings 122 may define a plurality of gaps G therebetween. As an example, in the absence of external pressure on the wire 114, the plurality of gaps G defined between the primary windings 122 may be oblique relative to the first longitudinal axis A1 circumscribed by the primary windings 122. Further, or instead, in instances in which the plurality of gaps G are along the first section 116 of the wire 114, the plurality of gaps G may facilitate providing the first section 116 of the wire 114 with greater rigidity (and, thus, a greater spring constant) than that of the second section 118 of the wire 114. Further, or instead, the plurality of gaps G along the first section 116 of the wire 114 may improve gripping properties of the first section 116 of the wire 114 to facilitate anchoring the implant 104 to the adjacent tissue of the vessel. For example, in some arrangements in which the plurality of gaps G are along the first section 116 of the wire, the plurality of gaps G may act as grip-like features, providing an increased surface area along the plurality of gaps G and/or providing another benefit that assists with anchoring. In some implementations, the plurality of gaps G of the first section 116 of the wire 114 may be equal or substantially equal (allowing for dimensional tolerances) for each instance of the plurality of gaps G. However, in other implementations, the size of the plurality of gaps G may vary along a section of the implant 104, as desired or required. Any other feature or property can be used to alter the rigidity and/or other aspects of the first section 116 of the wire 114 and/or of the second section 118 of the wire 114, either in lieu of or in addition to the inclusion of the plurality of gaps G along the corresponding portion of the wire 114.

According to some arrangements (e.g., those in which the plurality of gaps G are along the first section 116 of the wire 114), at least some of the plurality of gaps G may have an axial dimension greater than about 12 microns and less than about 130 microns. In some instances, a gap size of about 38 microns may provide advantageous characteristics for the first section 116 of the implant 104. In some instances, the second section 118 of the wire 114 may include the plurality of gaps G more gaps while, in other instances, the second section 118 of the wire 114 may not include any gaps. Further, in instances in which the first section 116 of the wire 114 and the second section 118 of the wire 114 each include the primary windings 122, the primary windings 122 of the first section 116 of the wire 114 may have a first outer diameter D1, and the primary windings 122 of the second section 118 of the wire 114 may have a second outer diameter D2. While the first outer diameter D1 and the second outer diameter D2 may be equal to one another in some instances, it shall be appreciated that the first outer diameter D1 may be different from (e.g., larger than or smaller than) the second outer diameter D2 in other instances. In instances in which the first section 116 of the wire 114 is non-circular, the first outer diameter D1 shall be understood to refer to a maximum outer cross-sectional dimension of the first section 116 in the delivery state. Similarly, in instances in which the second section 118 of the wire 114 is non-circular, the second outer diameter D2 shall be understood to refer to a maximum outer dimension of the second section 118 in the delivery state.

In some arrangements, the first section 116 of the wire 114 and the second section 118 of the wire 114 may be wound on a single cylindrical mandrel (not shown). The first section 116 of the wire 114 may have a first proximal portion 126 and a first distal portion 128, the second section 118 of the wire 114 may have a second proximal portion 130 and a second distal portion 132, and the first distal portion 128 may be coupled to the second proximal portion 130 at the coupling location 124 to form a single unitary implant from the first proximal portion 126 of the first section 116 of the wire 114 to the second distal portion 132 of the second section 118 of the wire 114. The first section 116 of the wire 114 and the second section 118 of the wire 114 may be secured to each other using any one or more connection methods or techniques. For instance, the first section 116 of the wire 114 and the second section 118 of the wire 114 may be secured to one another with one or more of a weld (e.g., a laser weld), an adhesive, or a sleeve at the coupling location 124. A weld may be particularly useful, as it does not introduce any new materials or material interactions and does not alter the aging of any existing materials in the first section 116 and/or the second section 118. Additionally, or alternatively, the first section 116 of the wire 114 and the second section 118 of the wire 114 may form a continuous outer surface along the coupling location 124. That is, at the coupling location 124, the connection between the first section 116 of the wire 114 and the second section 118 of the wire 114 may form a smooth transition between the first section 116 of the wire 114 and the second section 118 of the wire 114.

In general, the first section 116 of the wire 114 may be formed of a first material, and the second section 118 of the wire 114 may be formed of a second material, which may be the same as or different from the first material. In some implementations, the first section 116 of the wire 114 may include a platinum tungsten alloy. For example, the platinum tungsten alloy may include an alloy of 92% platinum, 8% tungsten (92/8 Pt/W), shape memory material having superelastic properties, other metals or alloys and/or any other material. Further, or instead, the first section 116 of the wire 114 may include a non-helical shape and/or materials that are not shape memory materials, as desired or required. The second section 118 of the wire 114 may additionally, or alternatively, include a platinum tungsten alloy and/or any other materials. For example, the second section 118 of the wire 114 may include platinum tungsten alloy including an alloy of 92% platinum and 8% tungsten (92/8 Pt/W). In other implementations, however, the implant 104 may include other alloys and/or other shape memory materials having superelastic properties, either in addition to or in lieu of platinum and tungsten.

In general, an axial length L, the first outer diameter D1, the second outer diameter D2, wire diameter WD, and/or the axial dimension between sequential turns or winds of the plurality of gaps G may be modified to accommodate a particular design and/or application or use. In some embodiments, the first outer diameter D1 of the first section 116 of the wire 114 and/or the second outer diameter D2 of the second section 118 of the wire 114 (when the implant 104 is in the delivery state, e.g., prior to release in the subject) may be about 0.25 mm to about 0.51 mm inches, with allowances for variations associated with manufacturing tolerances. In other implementations, however, the first outer diameter D1 and/or the second outer diameter D2 may be less than about 0.25 mm or greater than about 0.51 mm.

In some implementations, the first section 116 of the wire 114 may have a first wire diameter WD1, and the second section 118 of the wire 114 may have a second wire diameter WD2 that are approximately equal in size (allowing for differences associated with manufacturing tolerances), while in other implementations, the first wire diameter WD1 and the second wire diameter WD2 may be different from one another. In some instances, the first wire diameter WD1 of the first section 116 of the wire 114 may be greater than about 25 microns and less than about 260 microns. However, in other arrangements, the first wire diameter WD1 of the first section 116 of the wire 114 may be less than about 25 microns or greater than about 260 microns. By way of example, in some instances, the first wire diameter WD1 of the first section 116 of the wire 114 may be about 70 microns to about 76 microns. Further, or instead, the second wire diameter WD2 of the second section 118 may be greater than about 25 microns less than about 260 microns. In some instances, the second wire diameter WD2 of the second section 118 of the wire 114 may be about 51 microns, about 64 microns, or about 76 microns.

In some instances, the wire 114 may have a first length L1 in the delivery state within the lumen 110 of the catheter 102 and a second length L2 in the deployed state in the absence of external pressure on the wire 114. The first length L1 may be greater than the second length L2. Further, or instead, the first length L1 may vary based on the type of vascular abnormality that is being treated, the target peripheral vessel (e.g., the vessel diameter), the intended procedure, the age, health or other characteristics of the subject and/or the like. In some implementations, the first length L1 of the wire 114 may be 0.5 cm to 100 cm (e.g., 0.5 to 100, 0.5 to 75, 0.5 to 50, 1 to 40 cm, values between the foregoing, etc.).

In some implementations, the first length L1 of the wire 114 in the delivery state may vary in proportion (e.g., in a linear manner, in a non-linear manner, etc.) to the outer diameter DIM B of the at least one loop 120 formed by the first section 116 of the wire 114 in the absence of external pressure (in the deployed state). For example, larger values of DIM B for treating larger vessels may correspond to larger values of first length L1. In some implementations, the outer diameter DIM B of the at least one loop 120 and the first length L1 of the implant 104 may be chosen to at least partially occlude blood flow in the target vessel location peripheral to a vascular defect.

In general, the pusher member 108 may be movable within the lumen 110 of the catheter 102 to push the implant 104 in a direction parallel to the second longitudinal axis A2 defined by the lumen 110 of the catheter 102. In some instances, the pusher member 108 may include one or more markers 134 indicative of advancement of the implant 104 relative to the lumen 110 of the catheter 102.

The pusher member 108 may be releasable from the tether 106 with the first section 116 of the wire 114 and the second section 118 of the wire 114 in the deployed state outside of the lumen 110 of the catheter 102. For example, the tether 106 may be formed of one or more thermoplastic elastomers. In some arrangements, the tether 106 may include a thermoplastic elastomer, such as, for example, Engage™ polyolefin elastomer (available from Dow of Midland, Michigan, U.S.), a polyester strand (e.g., polyethylene terephthalate (PET)), and/or any other material. The diameter of the tether 106 may be 19 microns to 76 microns.

In some implementations, the system 100 may include one or more valves. For example, the system 100 may include a rotating hemostatic valve 136 in fluid communication with the lumen 110 of the catheter 102. The rotating hemostatic valve 136 may facilitate controlling the position of the pusher member 108. For example, the rotating hemostatic valve 136 may be actuatable to tighten about the pusher member to restrict movement of the pusher member 108 in the lumen 110 of the catheter 102. As a more specific example, the pusher member 108 may include a proximal fluorosafe marker and, when the proximal fluorosafe marker reaches a hub of the catheter 102 (e.g., microcatheter) used to deliver the implant 104, the RHV may be tightened about the pusher member 108 to restrict any further distal movement of the pusher member 108. Additionally, or alternatively, the system 100 may include a one-way valve 138 in fluid communication with the distal opening 112 of the catheter via the lumen 110 of the catheter 102, and the one-way valve 138 may be actuatable to control delivery of fluid (e.g., normal saline) through the distal opening 112 via the lumen 110 of the catheter 102.

As an example, the system 100 may provide a flush of solution (e.g., normal saline). Flushing (e.g., continuous or intermittent flushing) may advantageously decrease friction between the implant 104 and the lumen 110 of the catheter 102 and/or may reduce the possibility of clot formation and/or provide one or more other benefits. To prepare the system 100 for continuous flushing, the rotating hemostatic valve 136 may be attached to a hub 140 of a guide catheter 142. A three-way stopcock 144 may be attached to a side arm of the rotating hemostatic valve 136 and a line may be connected for continuous infusion of flush solution. Another instance of the rotating hemostatic valve 136 may be attached to a hub 146 of the catheter 102. The one-way valve 138 (e.g., a one-way stopcock) may be attached to the to the sidearm of the rotating hemostatic valve 136 attached to the hub 146 of the catheter 102 and a line for continuous flushing of appropriate solution may be connected to the one-way valve 138.

The one-way valve 138 may be opened and the catheter 102 may be flushed with sterile flush solution before the one-way valve 138 is closed. In some implementations, to minimize or at least reduce the risk of thromboembolic complications, it may be helpful to maintain a continuous infusion of appropriate sterile flush solution into the guide catheter 142, an introducer sheath 148, and the catheter 102. In certain implementations, the continuous or substantially continuous flushing (e.g., using a flushing solution) may be provided via a pressurized bag or other pressurization source, for example, at a predetermined pressure (e.g., 300 mm Hg).

Having described various aspects of the system 100, attention is directed to an exemplary method of vascular treatment using the system 100. In particular, FIGS. 2A-2H are schematic representations of a temporal sequence of the exemplary method of vascular treatment including releasing the implant 104 and securing the implant at a target anatomical location within the vessel and at least partially occupy the anatomical vessel.

Referring now to FIGS. 1A-IF and 2A-2H, the exemplary method of vascular treatment using the system 100 may include advancing the implant 104, in the delivery state, through vasculature of a subject to a target anatomical location. The target location can include a peripheral vasculature location at or near a vascular abnormality, such as an aneurysm A (e.g., to, completely or at least partially, obstruct, occlude, redirect, etc., blood flow in vascular abnormalities of the peripheral vessels), a section of vasculature that is in need of vessel sacrifice, and/or any other location within the subject's anatomy. According to some arrangements, while disposed within the catheter 102, filamentary elements of layers of the implant 104 may take on elongated, non-everted configuration substantially parallel to each other and to the second longitudinal axis A2 of the lumen 110 of the catheter 102. Further, or instead, advancing implant 104 through the vasculature may include compressing (e.g., radially compressing) the implant 104 into the lumen 110 of the catheter 102 for intravascular delivery through the subject.

In some implementations, during a procedure, high quality, digital subtraction fluoroscopic road mapping may be used to determine and achieve correct guidance and placement of the implant 104 within the target location of the vasculature or other target location of the subject's anatomy. For example, in some arrangements, the guide catheter 142 may have an inner diameter large enough to allow for contrast injection while the catheter 102 (e.g., microcatheter) is being advanced to carry out the fluoroscopic road mapping during the procedure. Any other type of imaging or other technology may be additionally, or alternatively, used to assist with determining proper placement of the implant 104.

In certain implementations, the catheter 102 may be introduced into the vasculature of the subject using a percutaneous access point. The catheter 102 may be advanced to the cerebral vasculature of the subject, a peripheral vascular network of the subject, and/or any other anatomical location of the subject, as desired or required. The catheter 102 may be, for example, a reinforced catheter (e.g., a wire-reinforced microcatheter). Further, or instead, the catheter 102 may include one or more coatings, layers and/or other features. For example, in some instances, the catheter 102 may include an inner surface coating, such as, a polytetrafluorethylene (PTFE) and/or other thermoplastic coating. The catheter 102 may also, or instead, include one or more (e.g., 1, 2, 3, more than 3, etc.) radiopaque markers to assist with the advancement of the catheter 102 through the vasculature or other portion of the subject's anatomy.

In some instances, the guide catheter 142 and/or a guidewire may be used to facilitate advancement of the catheter 102 through the subject's anatomy to the target location. The catheter 102 may be advanced within the subject's intravascular network until the distal opening 112 of the catheter 102 is at or near the target location in the vasculature of the subject. The target location may be past (e.g., distal to) the aneurysm A. That is, at the target location, the distal opening 112 of the catheter 102 may be directed downstream of the peripheral vessel of the aneurysm A. Once the catheter 102 has been positioned, the guide catheter 142 may be removed.

After performing the fluoroscopic road mapping, a physician may measure and/or estimate the size of the lesion or vessel to be treated using, for example, pre-treatment angiograms (e.g., an angiographic assessment of the diameter of the parent vessel, peripheral vessel, lesion, and/or the like) and/or any other technology. In some instances, using this information (e.g., with or without considering other data, factors, etc.), the size of the implant 104 may be selected. The implant 104 may be advanced through the microcatheter 212 to the target vascular location distal to the aneurysm A. In some implementations, the implant 104 secured to the pusher member 108 may be pre-positioned within the catheter 102 (e.g., while the implant 104 is in the delivery state) prior to introduction of the catheter 102 into the vasculature. Alternatively, the implant 104 may be passed into a proximal opening of the lumen 110 of the catheter 102 after the catheter 102 is positioned within the body of the subject.

The implant 104 may be advanced distally towards the target vascular location through the distal opening 112 of the lumen 110 of the catheter 102. The implant 104 may be advanced by advancing the pusher member 108 within the lumen 110 of the catheter 102 in a smooth, continuous motion. The implant 104 may, for example, be advanced until the proximal end of the pusher member 108 contacts or otherwise interfaces the proximal end of the introducer sheath 148. After confirming the correct position of the pusher member 108, the rotating hemostatic valve may be loosened, and the introducer sheath 148 may be retracted from the rotating hemostatic valve 136.

In some implementations, a physician may locate the markers (e.g., fluorosafe markers) towards the proximal end of the pusher member 108. The implant 104 may be further advanced until the pusher member 108 is at least partially inside the rotating hemostatic valve 136 on the hub 146 of the catheter 102. The pusher member 108 may be further advanced until the fluorosafe markers approach the rotating hemostatic valve 136. In some arrangements, the fluorosafe markers reaching the rotating hemostatic valve 136 may indicate that the implant 104 is at or near the distal opening 112 of the catheter 102, and fluoroscopic guidance may be initiated.

The exemplary method of vascular treatment using the system 100 may include releasing the first section 116 of the wire 114 from the delivery state to the deployed state including the at least one loop 120. For example, once the distal opening 112 of the catheter 102 is positioned in at a location adjacent to a vascular defect, the implant 104 may be advanced distally beyond the distal opening 112 of the catheter 102, thus allowing the first section 116 of the wire 114 to begin to assume a three-dimensional or implanted shape including at the at least one loop 120. For example, using fluoroscopic guidance, the implant 104 may be slowly advanced out of the catheter 102 until desirable placement of the first section 116 of the wire 114 in the deployed state is achieved.

Additionally, or alternatively, the exemplary method of vascular treatment using the system 100 may include securing the at least one loop 120 to the target anatomical location. That is, as the implant 104 emerges from the distal opening 112 under the axial force of the pusher member 108 moving distally along the lumen 110, the implant 104 may start to assume a non-elongated or implanted (e.g., non-linear) state within the target vascular location. In some embodiments, the first section 116 of the catheter 102 may emerge from the distal opening 112 of the catheter 102 and begin to form the at least one loop 120 in the deployed state such that the first section 116 of the wire 114 in the deployed state may act as an anchor at the target vascular location, past the vascular defect (e.g., past the aneurysm A), to prevent or reduce the likelihood that the implant 104 will detach and/or otherwise undesirably move (e.g., migrate) from the target vascular location, even in high flow scenarios.

Further, or instead, the exemplary method of vascular treatment using the system 100 may include, with the at least one loop 120 secured to the target anatomical location, releasing the second section 118 of the wire 114 from the delivery state to the deployed state such that the second section 118 of the wire 114 has a non-linear shape at least partially occupying the anatomical vessel. That is, once the first section 116 of the wire 114 is anchored, the pusher member 108 may be further distally advanced in the lumen 110 of the catheter 102 such that the second section 118 of the implant 104 may begin to assume a non-linear shape associated with the deployment state of the second section 118 of the implant 104. As the implant 104 is further advanced in the distal direction, the relative flexibility of the second section 118 of the implant 104 may facilitate at least partially "packing" or occupying a volume of the anatomical vessel at or near the target vascular location. In some instances, the catheter 102 may be retracted proximately until the implant 104 at least partially occupies the target vascular location outside of the vascular defect (e.g., a location outside of the aneurysm A). However, in other embodiments, the catheter 102 is not retracted while the implant 104 is being deployed, as desired or required by a particular application or use.

Figure 2B:
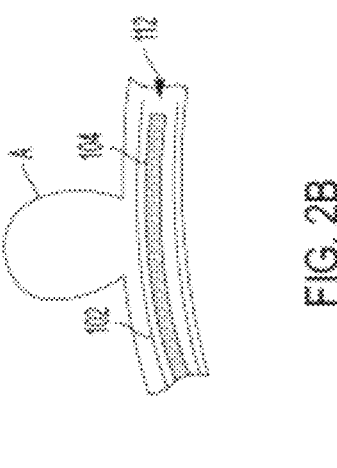
FIGS. 2A-2H are schematic representations of a temporal sequence of vascular treatment including releasing the implant of FIG. 1A and securing the implant at a target anatomical location within the vessel and at least partially occupy the anatomical vessel.
Figure 2A:
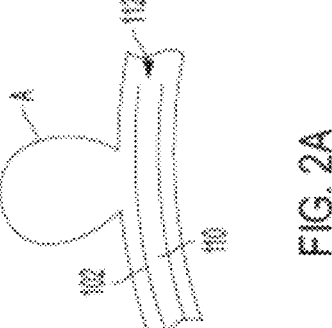
Figures 2C, 2D:
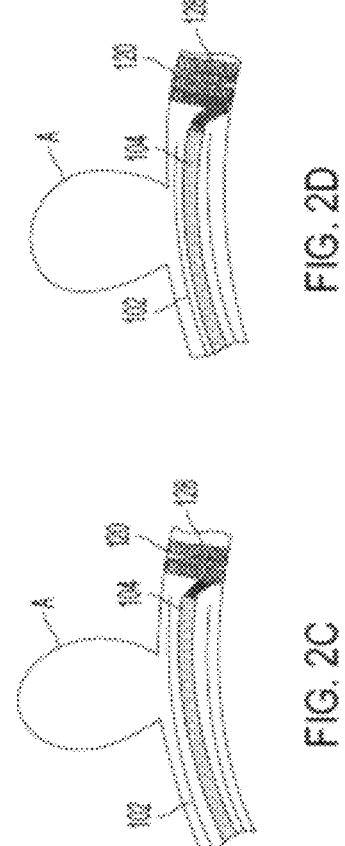
Figure 2F:
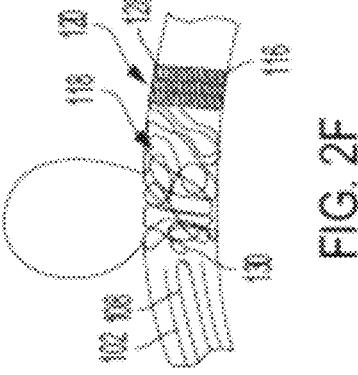
Figure 2E:
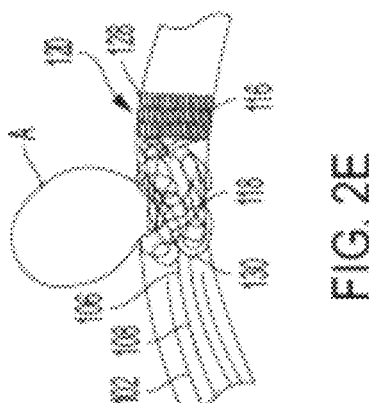
Figure 2H:
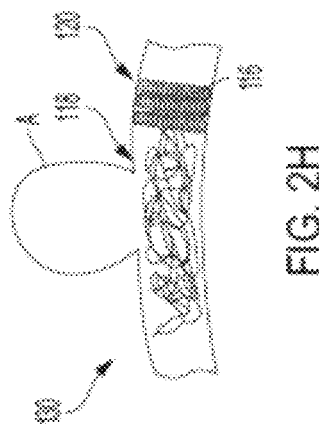

According to some embodiments, the implant 104 may be advanced until a detachment zone (e.g., the tether 106) is positioned outside (e.g., immediately outside of the distal opening 112) of the catheter 102 (see, e.g., FIG. 2E). There may exist some visual indication of this position when using imaging technologies. For example, the one or more markers 134 on the pusher member 210 may be adjacent to the distal side of a proximal radiopaque marker 150 on the catheter 102.

Figure 2G:
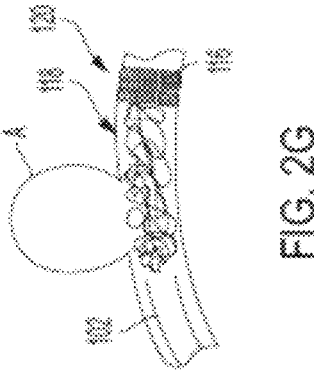

In some implementations, once the implant 104 is pushed out of the distal opening 112 of the catheter 102, the second distal portion 132 of the second section 118 of the wire 114 may axially contract (e.g., towards the second proximal portion 130), such that the second section 118 assumes a nonlinear shape (e.g., a three-dimensional configuration) within the target anatomical vessel. However, any other method or technique may be used to advance, deliver and/or deploy the implant 104 to a desired anatomical location of the subject, as desired or required. Once the implant 104 endovascularly obstructs or occludes blood flow in the target anatomical vessel, the catheter 102 may be removed from the subject, as shown in FIG. 2G.

With the implant 104 positioned at the target location with the detachment zone positioned outside of the catheter 102, the rotating hemostatic valve 136 may be tightened around the pusher member 108 to prevent or reduce the likelihood of movement of the implant 104. The operator may verify (e.g., once, repeatedly, etc.) that the distal end of the pusher member 108 is not under stress before coil detachment. This verification may be desired or required to reduce or eliminate the likelihood that axial compression or tension may result in the tip of the catheter 102 moving during detachment of the implant 104 to cause the vascular defect (e.g., aneurysm A) or a vessel to rupture.

Additionally, in some implementations, the implant 104 may be observed (e.g., under fluoroscopy or other imaging technology) following the placement and prior to the detachment of the implant 104 from the tether 106. This may help decrease or eliminate the likelihood of undesirable movement of the implant 104 after the completion of the procedure. In some instances, undesirable movement may indicate that the size of implant 104 is not suitable. In those circumstances, the implant 104 may be removed and replaced with another instance of implant 104 that is more appropriately sized for the particular procedure.

Once there are no issues with the placement of the implant 104, in some arrangements, the pusher member 108 may be detached from the tether 106 coupled to the second section 118 of the wire 114. Such detachment may be accomplished using any known method, such as, for instance, using heat or electrical energy to melt the tether, cutting or otherwise mechanically compromising the tether, chemically compromising the tether, and/or the like. Following detachment, the pusher member 108 may be removed from the catheter 102. For example, prior to removal of the pusher member 108, the rotating hemostatic valve 136 may be loosened and the pusher member 108 may be retracted (e.g., slowly) while confirming (e.g., under fluoroscopy or using other imaging technologies) that there is no movement of the implant 104 (e.g., or that any movement is within an acceptable tolerance).

As noted above, the microcoils and/or other implants disclosed herein can be detachable for purposes of delivery and implantation into a desired anatomical location. Any of a variety of known detachment methods or techniques can be used to deliver the implant within a desired anatomical location, as desired or required. Though detachment systems can include some dynamic process, some systems involve more physical movement of the system than others. For example, mechanical detachment systems, using pressure, unscrewing, axial pistoning release and/or the like may cause a finite amount of movement of the implant 104 at the target anatomical location during detachment. In some arrangements, non-mechanical detachment systems (e.g., chemical, temperature, electrolytic, etc.) may include less movement but may, in some cases, result in less consistency. However, in certain arrangements, such systems often suffer from less consistency. Though electrical isolation of the implant 104 itself may aid in lower average detachment times of the implant 104, there may still exist some inconsistency in how quickly the implant 104 may detach. Additionally, or alternatively, a single large detachment time may risk instability during the detachment (e.g., due to movement of the subject, other factors, etc.) of the implant 104. Some detachable systems may include a particular structure at a junction between the pusher member 108 and the implant 104.

While certain aspects of implants, systems, and methods of vascular treatment have described, other aspects of implants, systems, and methods of vascular treatment may be additionally or alternatively possible.

Figure 3:
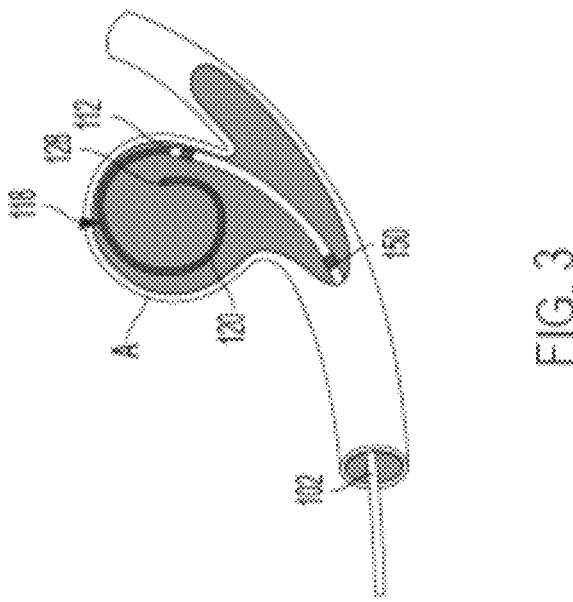
FIG. 3 is a schematic representation of vascular treatment including releasing the implant of FIG. 1A to secure the implant at a target anatomical location within an aneurysm of an anatomical vessel and at least partially occupying the aneurysm of the anatomical vessel.

As an example, while implants have been described as being deployed with the first section of the wire at least partially occupying a volume of an anatomical vessel, other types of deployment are additionally or alternatively possible. For example, referring now to FIG. 3, the first section 116 of the wire 114 may be deployed within the aneurysm A itself such that the at least one loop 120 may anchor within the aneurysm A. Additionally, or alternatively, it shall be appreciated that the implant 104 may be delivered to other vascular locations, such as an organ or the like.

As another example, while sections of the implant 104 has been described as being formed of a single alloy wound about the first longitudinal axis A1, it shall be appreciated that any one or more of the sections of the implant may include and inner member and/or one or more outer members, coating, and/or coverings.

In some embodiments, the implant 104 may include only a single alloy or other member that is wound about an axis. However, in other configurations, as noted above, the first section 116 of the wire 114 and/or second section 118 of the wire 114 may include an inner member and/or one or more outer members, coatings and/or coverings. For example, the first section 116 of the wire 114 and/or the second section 118 of the wire 114 may include an inner core or wire member and an outer wire member or covering. The outer wire member may surround and cover, at least partially, the inner or core wire member. In some instances, the outer wire member may be wound (e.g., helically) around the outside of the core wire. In some arrangements, one or more exterior layers or coatings may be positioned along the outside of both the outer wire member and the core wire.

Figure 4A:
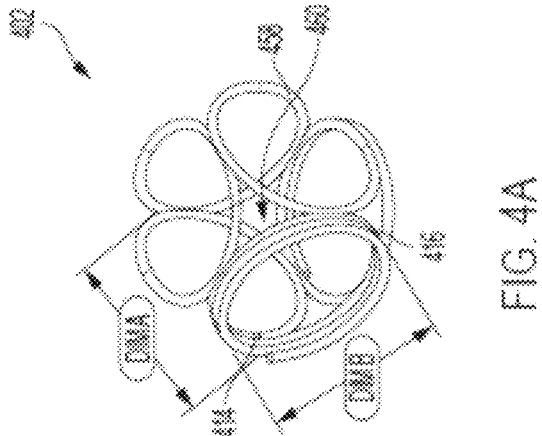
FIG. 4A is a perspective view of an implant including a wire having a first section and a second section, the wire shown in a deployed state in the absence of external force on the wire with the first section of the wire including at least one loop and the second section of the wire having a predetermined three-dimensional shape.
Figures 4B, 4C:
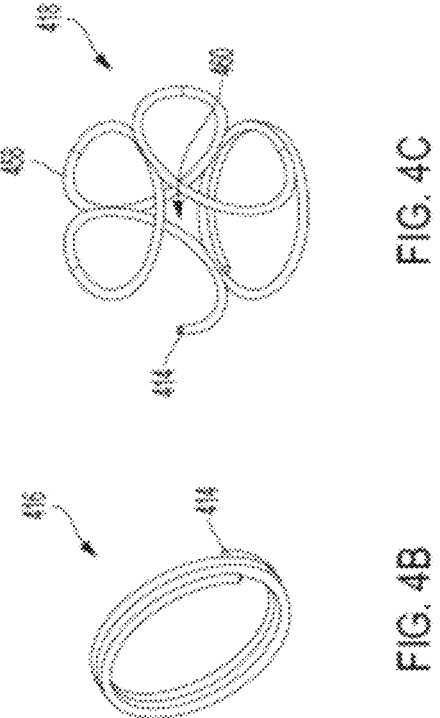
FIG. 4B is a perspective view of the first section of the wire of the implant of FIG. 4A, the first section of the wire shown in the deployed state in the absence of external force on the wire.
FIG. 4C is a perspective view of the second section of the wire of the implant of FIG. 4A, the second section of the wire shown in the deployed state in the absence of external force on the wire.

As yet another example, while implants have been described as including a second section that is packable, other configurations of the second section are additionally, or alternatively, possible. For example, referring now to FIGS. 4A, 4B, and 4C, an implant 404 may include a wire 414 having a first section 416 and a second section 418. For the sake of clear and efficient description, 100-series elements described above and having the same last two digits as 400-series element numbers in the portion of the description associated with FIGS. 4A-4C shall be understood to be analogous to or interchangeable with one another, unless otherwise explicitly made clear from the context, and, therefore, are not described separately from one another, except to note differences or to emphasize certain features. Thus, for example, the first section 416 of the wire 414 shall be understood to be analogous to the first section 116 of the wire 114 described above with respect to FIGS. 1A-IF and 2A-2H.

In the deployed state of the wire 414, the first section 416 of the wire 414 may secured the implant 104 at a target anatomical location according to the various techniques described herein, and the second section 418 of the wire 414 may have a predetermined three-dimensional shape in the absence of an external force on the second section 418 of the wire 414. For example, the predetermined three-dimensional shape of the second section 418 of the wire 414 may include one or more loops 458. For example, the predetermined three-dimensional shape formed by the one or more loops 458 of the second section 418 of the wire 414 in the deployed state may define a cavity 460 such that the second section 418 in the deployed state acts as a frame.

In some implementations, by way of example, the one or more loops 458 of the second section 418 of the wire 414 in the deployed state may have a diameter DIM A while the first section 416 of the wire 414 may have at least one loop 120 having a diameter DIM B in the deployed state. In some embodiments, the diameter DIM A of the one or more loops 458 in the second section 418 of the wire 414 may be 2 to 25 mm (e.g., 2 to 25, 3 to 20, 4 to 15, 5 to 10 mm, values between the foregoing, etc.). In some implementations, the diameter DIM A of the one or more loops 458 of the wire 414 may be equal or substantially equal to (e.g., within 0 to 5%, 0 to 10% of, within +/–1 mm or 2 mm of, etc.) the diameter DIM B of the at least one loop 120 of the first section 416 of the wire 414.

Figure 1F:
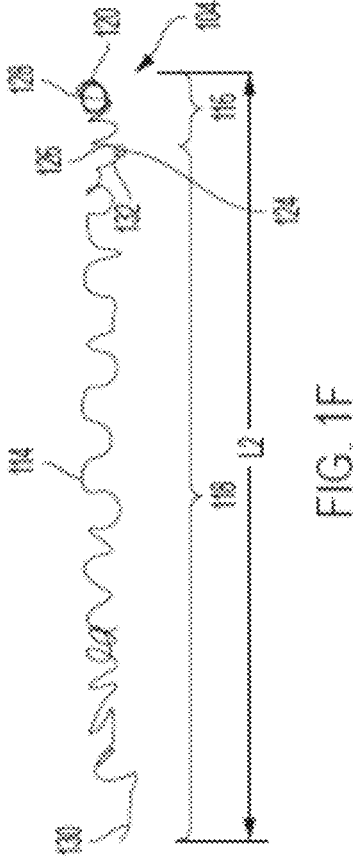
FIG. 1F is a schematic representation of the first section and the second section of the implant of FIG. 1A in the deployed state without external pressure on the wire.

As another example, while implants have been described as having a first section and a second section coupled to one another at a coupling location (e.g., the coupling location 124 shown in FIGS. 1C and 1F), it shall be appreciated that the first section of the wire and the second section of the wire of any one or more of the various different implants described herein may be collectively monolithic—that is, without a coupling location-such that the implant is a single member.

According to an aspect, an implant for vascular treatment may include a wire having three or more sections, with adjacent sections having different stiffnesses and/or other properties to facilitate treating an aneurysm with a single instance of the wire.

Referring now to FIGS. 5A-5E, a system 500 for vascular treatment may include a catheter 502, an implant 504, a tether 506, and a pusher member 508. The catheter 502 may define a lumen 510 and a distal opening 512 in fluid communication one another. The implant 504 may include a wire 514 having at least three sections 516, 518, 519 (referred to herein collectively as "the three or more sections 516, 518, 519" or individually as "the first section 516," "the second section 518," and "the third section 519") coupled to one another and positionable in the lumen 510. As described in greater detail below, each adjacent pair of the at least three sections 516, 518, 519 may have stiffness varying therebetween. The tether 506 may be coupled to the wire 514, and the pusher member 508 may be detachably coupled to the wire 514 via the tether 506. The pusher member 508 may be advanceable in the lumen 510, with advancement of the pusher member 508 moving at least one of the at least three sections 516, 518, 519 of the wire 514 through the distal opening 512 of the catheter 502 to a deployed state defining a volume, into which at least another one of the at least three sections 516, 518, 519 of the wire 514 is packable to occupy at least a portion of an anatomical vessel of a subject. For the sake of clear and efficient description, 100-series elements and 400-series elements described above and having the same last two digits as 500-series element numbers in the portion of the description associated with FIGS. 5A-5C shall be understood to be analogous to or interchangeable with one another (unless otherwise explicitly made clear from the context) and, therefore, are not described separately from one another, except to note differences or to emphasize certain features. Thus, for example, the first section 516 of the wire 514 shall be understood to be analogous to the first section 116 of the wire 114 described above with respect to FIGS. 1A-1F and 2A-2H and/or analogous to the first section 416 of the wire 414 described above with respect to FIGS. 4A-4C, unless a contrary intent is explicitly indicated or made clear from the context.

As compared to treating aneurysms (e.g., a side wall aneurysm) or vessel occlusion using multiple coils, the wire 514 having the at least three sections 516, 518, 519 may reduce the time required for treatment, given that only a single instance of the wire 514 needs to be tracked while the at least three sections 516, 518, 519 provide functionality of multiple coils. For example, in some treatments, separate coils may be used for framing, filling, and/or finishing. Each of these coils must be tracked separately to the treatment site, and this adds time to the procedure for treating aneurysms and/or vessel occlusion. Stated differently, the implant 504 including the wire 514 having the at least three sections 516, 518, 519 may facilitate achieving framing, filling, and/or finishing with fewer coils—and in some cases, only a single coil-thus reducing treatment times as compared to using dedicated coils for each of framing, filling, and/or finishing. Further, or instead, as compared to the use of multiple coils deployed from a catheter at a treatment site, the wire 514 including the at least three sections 516, 518, 519 for framing, filling, and/or finishing has only a single tail and, for at least this reason, may reduce the risk of tail herniation into an artery of a patient and/or may reduce risk of perforation, as compared to treatments using multiple coils.

In certain implementations, the first section 516, the second section 518, and the third section 519 of the wire 514 of the implant 504 may be movable from a delivery state to a deployed state in response to removal of external pressure on the wire 514. In the delivery state (e.g., in the lumen 510 of the catheter 502), the first section 516, the second section 518, and the third section 519 may collectively define a longitudinal axis L, with the second section 518 longitudinally disposed between the first section 516 and the third section 519. In the deployed state, the first section 516 may be securable to a target anatomical location of a subject with the first section 516 defining a first volume 551 and at least the second section 518 packable into the first volume 551 to occupy at least a portion of an anatomical vessel of the subject. The second section 518 of the wire 514 may have stiffness differing from respective stiffnesses of the first section 516 and the third section 519 of the wire 514 which, among other things, may facilitate achieving consistent and reliable deployment states of the at least three sections 516, 518, 519 relative to one another and relative to the treatment site to achieve functionality of framing, filling, and finishing as necessary or desirable for carrying out treatment while using only a single instance of the wire 514. As an example, the second section 518 may be less stiff (softer) than the first section 516 and, further, or instead, may be stiffer than the third section 519, with such variation in stiffness facilitating packing the second section 518 into the first section 516 and packing the third section 519 into the second section 518 packed into the first section 516 such that the first section 516, the second section 518, and the third section 519 to occupy an aneurysm and/or to occlude a vessel.

In general, in the deployed state and in the absence of external pressure, the first volume 551 defined by the first section 516 may be any shape that is maintainable as a frame substantially occupying the overall shape of the aneurysm being treated or vessel being occluded and providing support at the treatment site, with deviations from full occupation corresponding to irregularities in shape at the treatment site. For example, in the deployed state and in the absence of external pressure, the first volume 551 of the first section 516 may be in the shape of a box. As compared to other shapes, the first volume 551 of the first section 516 in the shape of a box may be advantageously provide support—namely, framing—at the treatment site in any orientation while also being conformable to an irregular shape of the treatment site.

Further, or instead, in the deployed state, the first volume 551 of the first section 516 may be accessible for packing with the second section 518 of the implant 504, even with the first volume 551 deformed in an irregular shape of the treatment site. As an example, in the deployed state, the first section may include at least one loop 520 defining the first volume 551. In the deployed state, the at least one loop 520 of the first section 516 may facilitate maintaining an open area through which the second section 518 may be packable into the first volume 551 of the first section 516. Further, or instead, the second section 518 may be packable into the first volume 551 of the first section 516 with the second section 518 defining a second volume 552. That is, returning to the example in which the first volume 551 of the first section 516 is in the shape of a box, the second volume 552 of the second section 518 may be packable into the first volume 551 with the second volume 552 of the second section 518 in the shape of a second box, smaller than the shape of the box of the first volume 551 of the first section 516. Continuing with this example, it shall be appreciated that the third section 519 may be packed into the second volume 552, where the third section 519 may be nominally in the shape of a box (allowing for compliance with irregularities in shape of the treatment site) in the deployed state. As a specific example, in the deployed state, the first section 516 may be a 7 mm box coil, the second section 518 may be a 5 mm box coil, and the third section 519 may be a 2 mm box coil.

While the third section 519 may be a box coil in some implementations, it shall be appreciated that in certain implementations other shapes of the third section 519 are additionally, or alternatively possible. For example, for aneurysm treatment, the first section 516 may be positionable in the first volume 551 disposed in the aneurysm of the anatomical vessel, and the third section 519 may be packable into a neck of the aneurysm to facilitate maintaining the first section 516 and the second section 518 in place within the aneurysm.

In general, the at least three sections 516, 518, 519 may have any respective lengths as may be useful for a given treatment and in accordance with the respective roles to be carried out by each of the at least three sections 516, 518, 519 during each treatment. For example, in the delivery state, the first section 516 may be longer than the second section 518, and the second section 518 may be longer than the third section 519.

In general, respective stiffnesses of the first section 516, the second section 518, and the third section 519 may be a function of one or more geometric parameters and/or material properties of each respective section. For example, as described in greater detail below, the respective stiffnesses of the first section 516, the second section 518, and the third section 519 may be varied by varying wire diameter of the wire 514, geometry of primary windings of the wire 514, and/or the modulus of rigidity of material forming the wire 514 along the at least three sections 516, 518, 519 of the wire 514.

In some implementations, the wire 514 may have a first wire diameter WD1 along the first section 516, a second wire diameter WD2 along the second section 518, and a third wire diameter WD3 along the third section. While the first wire diameter WD1, the second wire diameter WD2, and the third wire diameter WD3 may be the same in some instances, it shall be appreciated that variation of the wire diameter between at least two of the first section 516, the second section 518, or the third section 519 may facilitate imparting variation in stiffness between at least two of the sections. As an example, the first section 516, the second section 518, and the third section 519 may be formed of the same material (e.g., to facilitate welding the sections together) such that the first section 516, the second section 518, and the third section 519 have the same material properties-specifically, the same modulus of rigidity. Continuing with this example, with the same modulus of rigidity in each of the at least three sections 516, 518, 519, it shall be appreciated that variation of at least two of the first wire diameter WD1, the second wire diameter WD2, and the third wire diameter WD3 may have a direct relationship to variation in stiffness between the at least three sections 516, 518, 519. As may be appreciated from the foregoing, the modulus of rigidity of the wire 514 may additionally, or alternatively, vary between at least two of the first section 516, the second section 518, or the third section 519 to facilitate achieving a target variation in stiffness between the at least three sections 516, 518, 519.

In certain implementations, the wire 514 may include primary windings 522 along at least one of the first section 516, the second section 518, and the third section 519. In the delivery state, the primary windings 522 may circumscribe the longitudinal axis L such that the longitudinal axis L is the center axis of the primary windings 522. That is, the primary windings 522 may facilitate accommodating the implant 504 in the delivery state in the catheter 502 within an efficient length of the catheter 502 and, further or instead, may facilitate rapidly deploying the implant 504.

Additionally, or alternatively, variations in geometry of the primary windings 522 may facilitate achieving target variations in stiffness between the at least three sections 516, 518, 519. For example, the primary windings 522 may have a first outer diameter D1 along the first section 516, a second outer diameter D2 along the second section 518, and a third outer diameter D3 along the third section 519. In the absence of external pressure on the primary windings 522, an outer diameter of the primary windings 522 may vary between at least two of the first section 516, the second section 518, or the third section 519, as may be useful for varying stiffness between the at least three sections 516, 518, 519. That is, the first outer diameter D1 along the first section 516 may be less than the second outer diameter D2 along the second section 518 to facilitate forming the first section 516 with greater stiffness than that of the second section 518. Continuing with this example, the second outer diameter D2 along the second section 518 may be greater than the third outer diameter D3 along the third section 519 to facilitate forming the second section 518 with greater stiffness than that of the third section 519. Further, or instead, the primary windings 522 may define gaps G therebetween, and the size of the gaps G may vary between at least two of the first section 516, the second section 518, or the third section 519, with larger gap sizes facilitating achieving decreased stiffness (increased softness).

In certain implementations, as compared to an implant having only a single stiffness, abrupt or gradual changes in differences in stiffness between adjacent instances of the at least three sections 516, 518, 519 along the longitudinal axis L may form stress transition zones that may facilitate breaking the implant 504—that is, facilitating change in layup of the implant 504—according to the respective functions of each of the at least three sections 516, 518, 519 as the implant 504 is deployed from the catheter 502 at the treatment site. As an example, the second section 518 may have a proximal region 553 and a distal region 554. The first section 516 may be coupled to the distal region 554 of the second section at a first stress transition zone 555. Further, or instead, the third section 519 may be coupled to the proximal region 553 of the second section 518 at a second stress transition zone 556. The first stress transition zone 555 and/or the second stress transition zone 556 may include any one or more of various types of mechanical couplings compatible with the respective materials of the at least three sections 516, 518, 519 while accommodating stress differences at the first stress transition zone 555 and/or at the second stress transition zone 556. Thus, for example, at least one of the first stress transition zone 555 or the second stress transition zone 556 may include a respective weld (e.g., a laser weld). Further, or instead, the first stress transition zone 555 and/or the second stress transition zone 556 may include a sleeve crimped to the second section 518 and at least one of the first section 516 along the first stress transition zone 555 or the third section 519 along the second stress transition zone 556, as the case may be. Still further, or instead, at least one of the first stress transition zone 555 or the second stress transition zone 556 may include glue, thread, or a combination thereof.

Having described various aspects of implants including three or more sections and having stiffness variations to facilitate vascular treatment using a single instance of a wire, attention is now directed to description of certain aspects of fabricating such implants for vascular treatment.

Figure 5A:
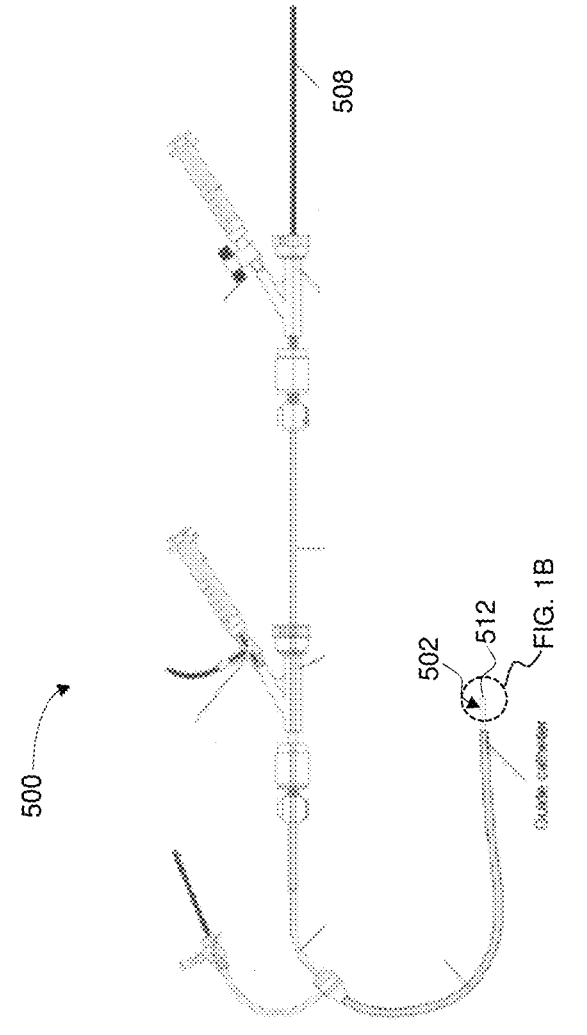
FIG. 5A is a schematic representation of a system for vascular treatment, the system including a catheter, an implant, a tether, and a pusher member, with the implant including a wire having three or more sections.
Figure 5B:
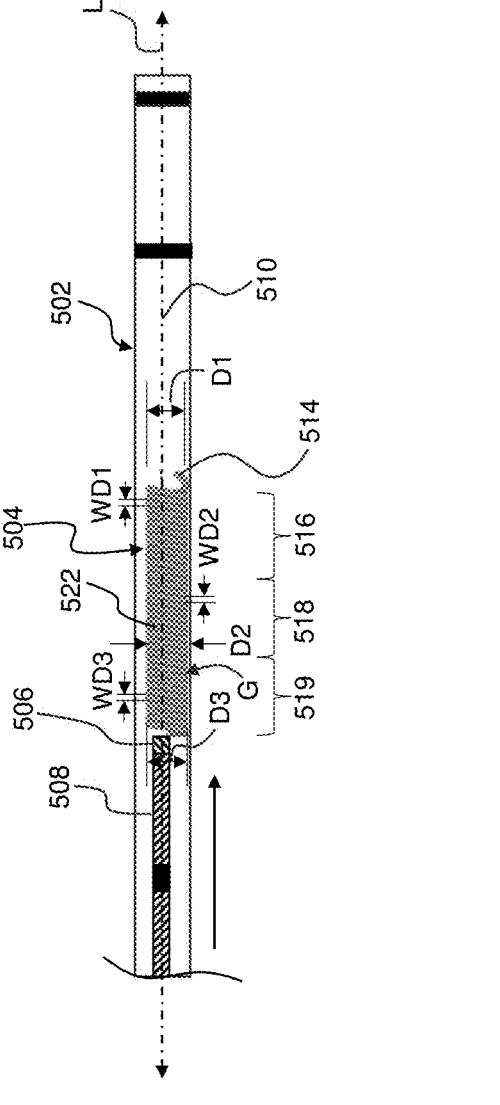
FIG. 5B is a schematic representation of a cross-section of a distal portion of the system of FIG. 5A as the pusher member moves the implant distally through the catheter.
Figure 5C:
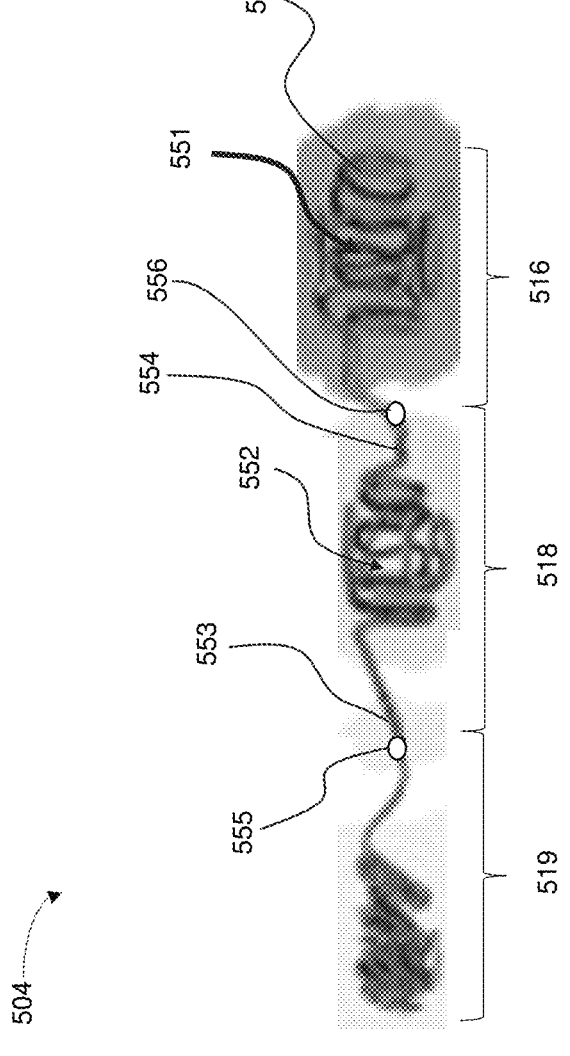
FIG. 5C is a schematic representation of the first section, the second section, and the third section of the implant of FIG. 5A in a deployed state without external pressure on the wire, shown with the first section heat-set and defining a first volume and with the second section heat-set and defining a second volume.
Figure 6:
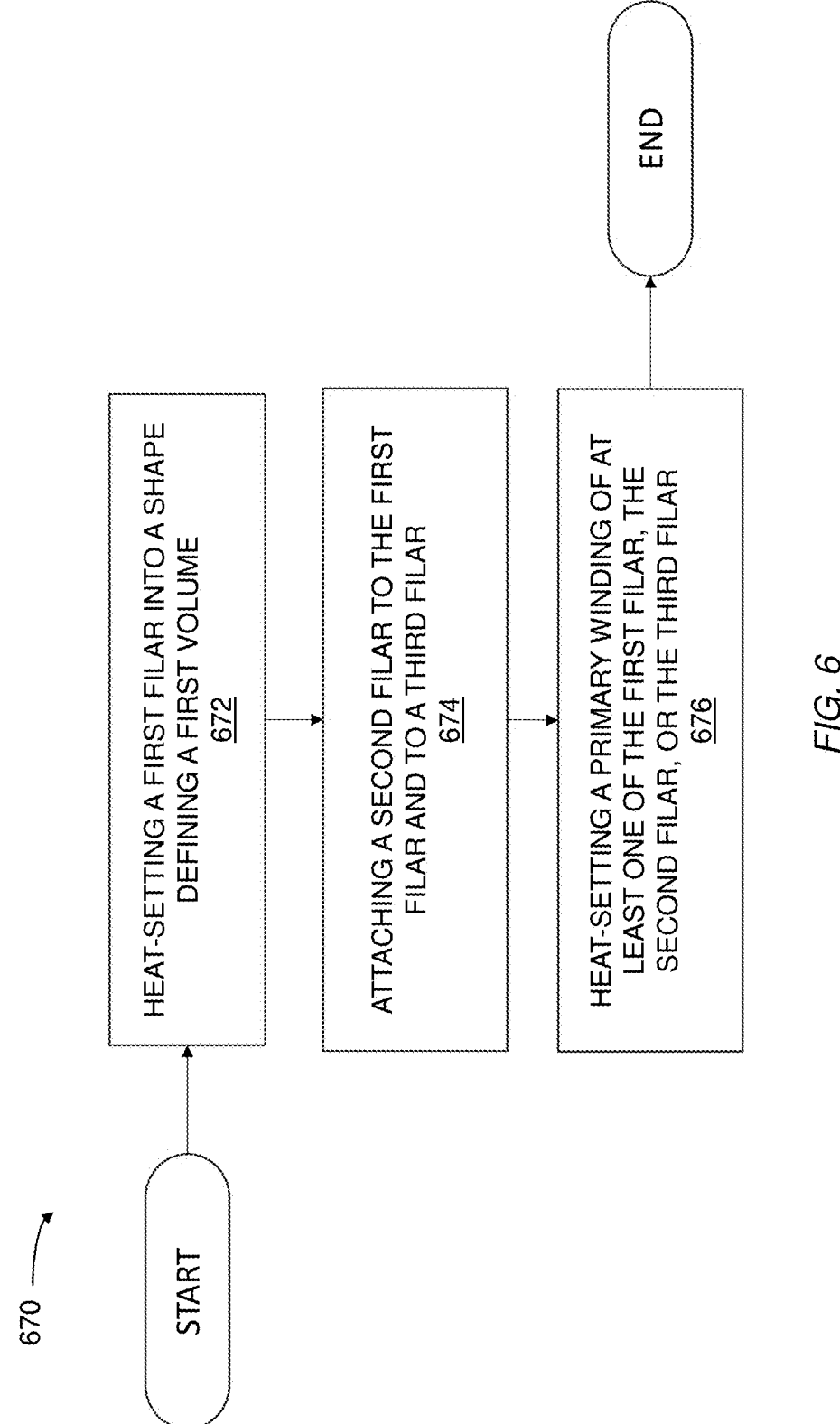
FIG. 6 is a flow chart of an exemplary method of fabricating an implant for vascular treatment.
Figure 7:
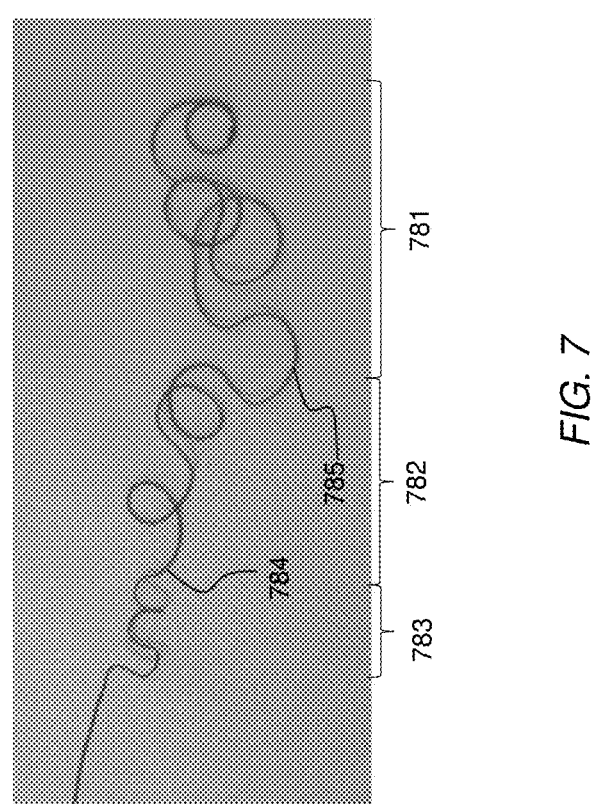
FIG. 7 is a schematic representation of a first filar, a second filar, and a third filar without external pressure and prior to heat-setting any of the sections according to the exemplary method of FIG. 6.

Referring now to FIGS. 6 and 7, an exemplary method 670 of fabricating an implant for vascular treatment is described. Unless otherwise specified or made clear from the context, it shall be understood that the exemplary method 670 may be used to fabricate a first filar 781, a second filar 782, and a third filar 783 into the implant 504 (FIGS. 5A-5C).

Figure 5D:
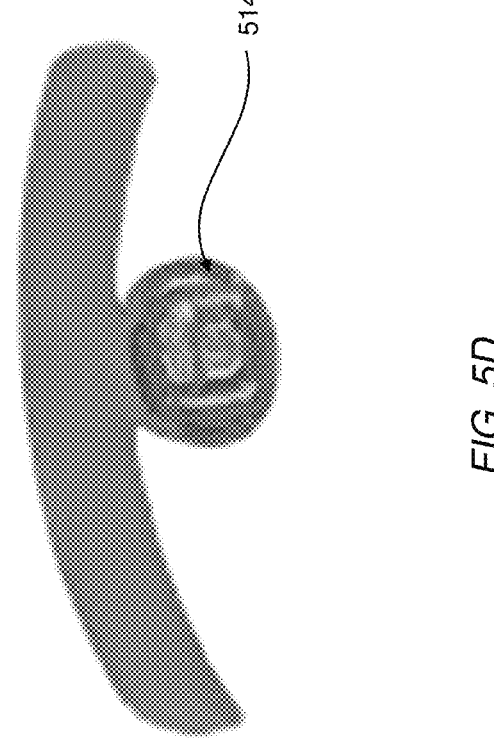
FIG. 5D is a schematic representation of the first section, the second section, and the third section deployed at a treatment site of a subject, with the second volume of the second section disposed in the first volume of the first section and with the third section filling the second volume.

As shown in step 672, the exemplary method 670 may include heat-setting the first filar 781 into a shape defining a first volume (e.g., the first volume 551 in FIG. 5D).

As shown in step 674, the exemplary method 670 may include attaching the second filar 782 to the first filar 781 and to the third filar 783, the second filar 782 differing in stiffness with respect to each of the first filar 781 and the third filar 783. The first filar 781, the second filar 782, and the third filar 783 may respectively form a first section, a second section, and a third section of a wire (e.g., the first section 516, the second section 518, and the third section 519 of the wire 514) movable, in response to removal of external pressure on the wire, from a delivery state to a deployed state in which the first section is securable to a target anatomical location of a subject with the first section defining the first volume and at least the second section packable into the first volume. For example, the second filar 782 may have a proximal portion 784 and a distal portion 785. Attaching the second filar 782 to the first filar 781 may include attaching the distal portion 785 of the second filar 782 to the first filar 781 to form a first stress transition zone. Further, or instead, attaching the second filar 782 to the third filar 783 may include attaching the proximal portion 784 to the third filar 783 to form a second stress transition zone. In general, the distal portion of the second filar 782 may be attached to the first filar 781 and the proximal portion of the second filar 782 may be attached to the third filar 783 according to any one or more of various techniques accommodating the stress associated with stiffness difference at each respective attachment. For example, attaching the distal portion 785 of the second filar 782 to the first filar 781 may include one or more of welding, gluing, tying, or crimping the first filar 781 and the second filar 782 to one another along the first stress transition zone. Further, or instead, attaching the third filar 783 to the second filar 782 may include one or more of welding, gluing, tying, or crimping the third filar 783 and the second filar 782 to one another along the second stress transition zone.

In certain implementations, at least some of the difference in stiffness at the first stress transition zone and at the second stress transition zone may be attributable to differences between the first filar 781, the second filar 782, and the third filar 783. For example, the first filar 781 may have a first diameter (first wire diameter), the second filar 782 may have a second diameter (second wire diameter), and third filar 783 may have a third diameter (third wire diameter), and at least two of the first diameter, the second diameter, and the third diameter differ from one another. Additionally, or alternatively, the first filar, the second filar, and the second filar may be formed from different materials, with the materials differing in modulus of rigidity and, thus, contributing to differences in stiffness at the first transition zone and the second transition zone.

As shown in step 676, the exemplary method 670 may further, or instead, include heat-setting a primary winding of at least one of the first filar 781, the second filar 782, or the third filar 783. Any one or more aspects of the respective primary winding described herein (e.g., respective outer diameters and/or gap sizes defined by windings) may be used to impart stiffness differences along the first transition zone and/or along the second transition zone.

While implants have been shown as including a wire having three sections, it shall be appreciated that this is for the sake of clear and efficient description and additional sections are additionally or alternatively possible.

Figure 8:
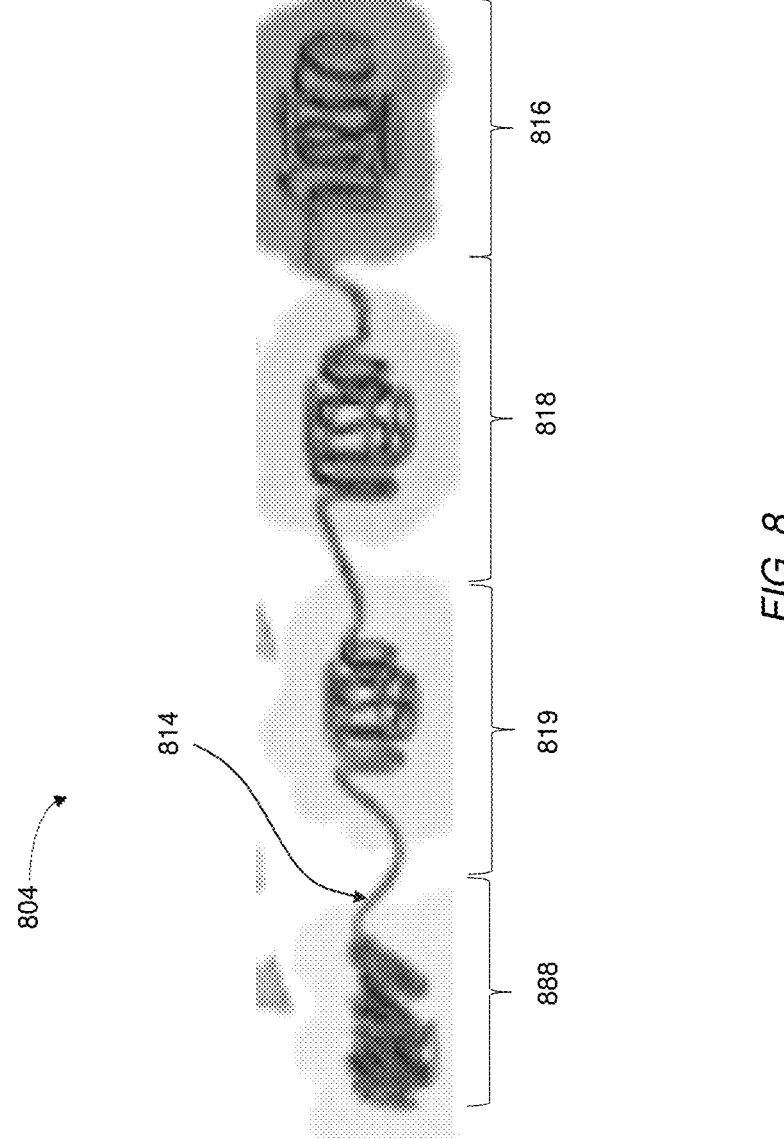
FIG. 8 is a schematic representation of a first section, a second section, a third section, and a fourth section of a wire of an implant in a deployed state without external pressure on the wire, shown with the first section heat-set and defining a first volume, with the second section heat-set and defining a second volume, and the third section heat-set and defining a second volume.

For example, referring now to FIG. 8, an implant 804 may a wire 514 having a first section 816, a second section 818, a third section 819, and a fourth section 888. For the sake of clear and efficient description, 100-series elements, 400-series elements, and 500-series elements described above and having the same last two digits as 800-series element numbers in the portion of the description associated with FIG. 8 shall be understood to be analogous to or interchangeable with one another (unless otherwise explicitly made clear from the context) and, therefore, are not described separately from one another, except to note differences or to emphasize certain features. Thus, for example, the first section 816 of the wire 514 shall be understood to be analogous to the first section 116 of the wire 114 described above with respect to FIGS. 1A-1F and 2A-2H, to be analogous to the first section 416 of the wire 414 described above with respect to FIGS. 4A-4C, and/or to be analogous to the first section 516 of the wire 514 described above with respect to FIGS. 5A-5D, unless a contrary intent is explicitly indicated or made clear from the context.

In certain implementations, in the delivery state, the third section 819 may be disposed between the second section 818 and the fourth section 888, and the fourth section 888 may be softer than the third section 819. That is, more generally, the proximal-most section of the wire 814 may facilitate coupling the wire 814 to a pusher member (e.g., the pusher member 508 in FIG. 5B) with a short, low-stiffness section that helps with stabilizing catheter kickback just before detachment of the wire 814. While considerations associated with stabilizing catheter kickback may make low stiffness useful in the proximal-most section of the wire 814, some stiffness in the proximal-most section of the wire 814 may be useful for reducing the likelihood of the proximal-most section of the wire inadvertently retracting into the catheter as the wire 814 is deployed according to any one or more of the various techniques described herein. Stated differently, stiffness of the proximal-most section of the wire 814 may be a balance between design considerations associated with stabilizing catheter kickback while reducing the likelihood of inadvertent retraction of the wire 814 into the catheter during deployment of the wire 814.

The method steps of the implementations described herein are intended to include any suitable method of causing such method steps to be performed, consistent with the patentability of the following claims, unless a different meaning is expressly provided or otherwise clear from the context. So, for example performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It will be appreciated that the methods and systems described above are set forth by way of example and not of limitation. Numerous variations, additions, omissions, and other modifications will be apparent to one of ordinary skill in the art. Absent an explicit indication to the contrary, the disclosed steps may be modified, supplemented, omitted, and/or re-ordered without departing from the scope of this disclosure. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims.

What is claimed is:

1. An implant for vascular treatment, the implant comprising:
a wire having a first section, a second section, and a third section movable from a delivery state to a deployed state in response to removal of external pressure on the wire,
in the delivery state, the first section, the second section, and the third section collectively defining a longitudinal axis with the second section longitudinally disposed between the first section and third section,
the second section of the wire having stiffness differing from respective stiffnesses of the first section and the third section, and
in the deployed state, the first section securable to a target anatomical location of a subject with the first section defining a first volume and the second section packable into the first volume to occupy at least a portion of an anatomical vessel of the subject, wherein the second section is less stiff than the first section and is stiffer than the third section.

2. The implant of claim 1, wherein, in the deployed state and in the absence of external pressure, the first volume of the first section is in the shape of a box.

3. The implant of claim 1, wherein, in the deployed state, the second section is packable into the first volume of the first section with the second section defining a second volume, and the third section is packable into the second volume of the second section within the first volume of the first section.

4. The implant of claim 1, wherein the first section is positionable with the volume disposed in an aneurysm of the anatomical vessel, and the third section is a packable into a neck of the aneurysm.

5. The implant of claim 1, wherein, in the delivery state, the first section is longer than the second section, and the second section is longer than the third section.

6. The implant of claim 1, wherein, in the deployed state, the first section includes at least one loop defining the volume.

7. The implant of claim 1, wherein the second section has a proximal region and a distal region, the first section is coupled to the distal region of the second section at a first stress transition zone, the third section is coupled to the proximal region of the second section at a second stress transition zone.

8. The implant of claim 7, wherein at least one of the first stress transition zone or the second stress transition zone includes a weld.

9. The implant of claim 7, wherein at least one of the first stress transition zone or the second stress transition zone includes glue, thread, or a combination thereof.

10. The implant of claim 7, wherein the wire has a wire diameter varying between at least two of the first section, the second section, or the third section.

11. The implant of claim 7, wherein the wire includes primary windings along at least one of the first section, the second section, and the third section.

12. The implant of claim 11, wherein, in absence of external pressure on the primary windings, an outer diameter of the primary windings varies between at least two of the first section, the second section, or the third section.

13. The implant of claim 11, wherein the primary windings define gaps therebetween, and the size of the gaps of the primary windings vary between at least two of the first section, the second section, or the third section.

14. The implant of claim 1, wherein modulus of rigidity of the wire varies between at least two of the first section, the second section, or the third section.

15. An implant for vascular treatment, the implant comprising:

a wire having a first section, a second section, and a third section movable from a delivery state to a deployed state in response to removal of external pressure on the wire, in the delivery state, the first section, the second section, and the third section collectively defining a longitudinal axis with the second section longitudinally disposed between the first section and third section, the second section of the wire having stiffness differing from respective stiffnesses of the first section and the third section, and in the deployed state, the first section securable to a target anatomical location of a subject with the first section defining a first volume and the second section packable into the first volume to occupy at least a portion of an anatomical vessel of the subject, wherein the second section has a proximal region and a distal region, the first section is coupled to the distal region of the second section at a first stress transition zone, the third section is coupled to the proximal region of the second section at a second stress transition zone, further comprising a sleeve crimped to the second section and at least one of the first section along the first stress transition zone or the third section along the second stress transition zone.

16. An implant for vascular treatment, the implant comprising:

a wire having a first section, a second section, and a third section movable from a delivery state to a deployed state in response to removal of external pressure on the wire, in the delivery state, the first section, the second section, and the third section collectively defining a longitudinal axis with the second section longitudinally disposed between the first section and third section, the second section of the wire having stiffness differing from respective stiffnesses of the first section and the third section, and in the deployed state, the first section securable to a target anatomical location of a subject with the first section defining a first volume and the second section packable into the first volume to occupy at least a portion of an anatomical vessel of the subject, further comprising a fourth section wherein, in the delivery state, the third section is disposed between the second section and the fourth section, and the fourth section is softer than the third section.

* * * * *